US009999509B2

(12) United States Patent
Dikovsky et al.

(10) Patent No.: US 9,999,509 B2
(45) Date of Patent: Jun. 19, 2018

(54) SYSTEM AND METHOD FOR FABRICATING A BODY PART MODEL USING MULTI-MATERIAL ADDITIVE MANUFACTURING

(71) Applicant: Stratasys Ltd., Rechovot (IL)

(72) Inventors: Daniel Dikovsky, Rehovot (IL); Stanislav Shtilerman, Modiln (IL)

(73) Assignee: Stratasys Ltd., Rehovot (IL)

( * ) Notice: Subject to any disclaimer, the term of this patent is extended or adjusted under 35 U.S.C. 154(b) by 510 days.

(21) Appl. No.: 14/358,092

(22) PCT Filed: Nov. 15, 2012

(86) PCT No.: PCT/IB2012/056462
§ 371 (c)(1),
(2) Date: May 14, 2014

(87) PCT Pub. No.: WO2013/072874
PCT Pub. Date: May 23, 2013

(65) Prior Publication Data
US 2014/0312535 A1 Oct. 23, 2014

Related U.S. Application Data (60) Provisional application No. 61/560,822, filed on Nov. 17, 2011.

(51) Int. Cl.
*A61B 17/56* (2006.01)
*A61F 2/30* (2006.01)
(Continued)

(52) U.S. Cl.
CPC ...... *A61F 2/30942* (2013.01); *A61C 13/0019* (2013.01); *B29C 67/0059* (2013.01);
(Continued)

(58) Field of Classification Search
CPC .................................................. B29C 67/0059
See application file for complete search history.

(56) References Cited

U.S. PATENT DOCUMENTS 5,454,069 A * 9/1995 Knapp ................... G06T 17/00
345/420
5,768,134 A 6/1998 Swaelens et al.
(Continued)

FOREIGN PATENT DOCUMENTS

JP 63-024478 1/1988
WO WO 2005/057436 6/2005
(Continued)

OTHER PUBLICATIONS

Hiller et al., "Tunable digital material properties for 3D voxel printers", Rapid Prototyping Journal, vol. 16 No. 4, 2010 p. 241-247.*
(Continued)

*Primary Examiner* — Galen H Hauth (57) ABSTRACT

A method for physically reconstructing a body part using multi-material additive manufacturing includes receiving image data of the body part in the form of arrays of voxels, each array of voxels representing image data pertaining to cross-section of the body part, translating the image data in the arrays of voxels to printable bitmap images representing combinations of modeling materials for reconstructing the body part, and dispensing the combinations of modeling materials responsive to the bitmap images in a layerwise manner.

19 Claims, 7 Drawing Sheets

(51) Int. Cl.
*B33Y 50/00* (2015.01)
*A61C 13/00* (2006.01)
*B29C 67/00* (2017.01)
*G06F 17/50* (2006.01)
*B33Y 70/00* (2015.01)
*B29L 31/00* (2006.01)
*A61B 5/055* (2006.01)

(52) U.S. Cl.
CPC .............. *B33Y 50/00* (2014.12); *G06F 17/50* (2013.01); *A61B 5/055* (2013.01); *A61F 2002/30948* (2013.01); *A61F 2002/30962* (2013.01); *A61F 2002/30985* (2013.01); *B29L 2031/7532* (2013.01); *B33Y 70/00* (2014.12)

(56) References Cited

U.S. PATENT DOCUMENTS

| | | |
|---|---|---|
| 8,509,933 B2 | 8/2013 | Steingart et al. |
| 8,817,332 B2 | 8/2014 | Wu |
| 2006/0105011 A1 | 5/2006 | Sun et al. |
| 2010/0124731 A1* | 5/2010 | Groscurth ................ A61C 9/00 433/213 |
| 2010/0140852 A1* | 6/2010 | Kritchman .......... B29C 67/0085 264/494 |
| 2010/0191360 A1 | 7/2010 | Napadensky et al. |
| 2012/0065755 A1* | 3/2012 | Steingart ............ A61C 13/0019 700/98 |

FOREIGN PATENT DOCUMENTS

| | | |
|---|---|---|
| WO | WO 2011/135496 | 11/2011 |
| WO | WO 2013/072874 | 5/2013 |

OTHER PUBLICATIONS

Notification of Office Action and Search Report dated Nov. 12, 2015 From the State Intellectual Property Office of the People's Republic of China Re. Application No. 201280065938.0.
Translation dated Dec. 16, 2015 of Notification of Office Action dated Nov. 12, 2015 From the State Intellectual Property Office of the People's Republic of China Re. Application No. 201280065938.0.
International Preliminary Report on Patentability dated May 30, 2014 From the International Bureau of WIPO Re. Application No. PCT/IB2012/056462.
International Search Report and the Written Opinion dated Apr. 8, 2013 From the International Searching Authority Re. Application No. PCT/IB2012/056462.
Hiller et al. "Tunable Digital Material Properties for 3D Voxel Printers", Rapid Prototyping Journal, XP002694093, 16(4): 33-44, Sep. 10, 2008. p. 38, Last Para-p. 40, Last Para.
Mironov et al. "Organ Printing: Tissue Spheroids as Building Blocks", Biomaterials, XP002694094, 30: 2164-2174, Jan. 26, 2009. Abstract, Figs.2, 4, 5.
Notice of Reasons for Rejection dated Oct. 25, 2016 From the Japan Patent Office Re. Application No. 2014-541799 and Its Translation Into English. (7 pages).
Office Action dated Mar. 28, 2018 From the Israel Patent Office Re. Application No. 234456 and Its Translation Into English. (7 pages).

* cited by examiner

SYSTEM AND METHOD FOR FABRICATING A BODY PART MODEL USING MULTI-MATERIAL ADDITIVE MANUFACTURING

RELATED APPLICATIONS

This application is a National Phase of PCT Patent Application No. PCT/IB2012/056462 having International filing date of Nov. 15, 2012, which claims the benefit of priority under 35 USC 119(e) of U.S. Provisional Patent Application No. 61/560,822 filed on Nov. 17, 2011. The contents of the above applications are all incorporated by reference as if fully set forth herein in their entirety.

FIELD OF THE INVENTION

The present invention, in some embodiments thereof, relates to multi-material Additive Manufacturing (AM) and, more particularly, but not exclusively, to tomographic based physical reconstruction of an object such as a body part with multi-material AM.

BACKGROUND OF THE INVENTION

AM methods are known to be used to fabricate models of three-dimensional objects, including biological organs. AM or Solid Freeform Fabrication (SFF) is a technology enabling fabrication of arbitrarily shaped structures directly from computer data via additive formation steps. The basic operation of any SFF system consists of slicing a three-dimensional computer model into thin cross sections, translating the result into two-dimensional position data and feeding the data to control equipment which fabricates a three-dimensional structure in a layerwise manner.

Methods for using tomography data, e.g. data provided by a Computer Tomography (CT) scanner or Magnetic Resonance Image (MRI) machine to physically reconstruct a biological organ by AM are also known. The tomography data typically includes grayscale image data of cross sections of the scanned biological organ. Typically, the tomography data is provided in a Digital Imaging and Communications in Medicine (DICOM) file format.

In known physical reconstructing methods, a Computer Aided Design (CAD) system is used to convert and/or translate the DICOM file to a three-dimensional computer model in the form of a StereoLithography (STL) file that can be read by AM devices. STL files only describe surface geometry of a three dimensional object without any representation of possible variations in color, texture and/or mechanical properties within the volume of the three dimensional object. Since variations within the volume cannot be represented with an STL file, much of the information included in the DICOM file is lost during the translation.

U.S. Pat. No. 5,768,134 entitled "Method for making a perfected medical model on the basis of digital image information of a part of the body" incorporated herein by reference in its entirety, describes a method for adding an artificial function element to a model of a body part based on digital image information, e.g. in a CT image prior to segmentation. As described therein, the artificial function element that is added is a function of the digital image information in the form in which all medical data are visible, before segmenting image data pertaining to the body part from the rest of the image. It is described by way of example that a function element, such as an opening indicating the place and direction for boring, can be added as a function of the image information showing additional elements surrounding the body part. It is also described that external information coming from the medical user may be added to the image information and the artificial functional element may also be a function of this additional external information.

US Patent Publication No. 20100191360 entitled "Solid freeform fabrication using a plurality of modeling materials," assigned to the common assignee and incorporated herein by reference in its entirety, describes inter alia a system and method for fabricating objects using two or more modeling materials in different predetermined combinations, wherein the combinations are produced by dispensing different modeling materials from different dispensing heads. The different modeling materials may be dispensed in different locations within a layer or may be dispensed in same location or adjacent locations so as to allow formation of a composite material.

There is also described a method for defining composite material structures without the need for standard CAD software in order to design the full three-dimensional structure. The method described includes performing a Boolean comparison between bitmaps representing the desired composite material structure and bitmaps produced by STL files representing the three-dimensional object. It is stated that by eliminating the need for standard CAD software for creating a bitmap representation of the desired composite material structure, the time that would be required for the design process is saved as well as computer memory resources which would usually be required in order to design three-dimensional structures and for the analysis of such three-dimensional structure during the building process.

It is further described that the two or more building and/or modeling materials can include a non-solidifiable material that remains in liquid, gel, paste or other non-solid or semi-solid form. Optionally, a second solidifiable material can fully surround or contain the non-solidifiable material during fabrication so that the non-solidifiable material can remain within the object, or alternatively be drained, burnt-out or otherwise removed once the process is complete. In this way it is described that a hollow or porous model can be provided.

SUMMARY OF THE INVENTION

According to an aspect of some embodiments of the present invention there is provided a system and method for translating tomography data of a body part into a printable bitmap image representing combinations of modeling materials that can be used to physically reconstruct the body part by multi-material AM. According to some embodiments of the present invention, a relationship between the tomography data and mechanical properties of tissue making up the body part is defined. In some exemplary embodiments, the combinations of modeling materials for reconstructing the body part are defined to mimic the different mechanical properties as represented by the tomography data. Optionally, the combination of modeling materials include one or more predefined structures designed to enhance representation of one or more of a physical and/or mechanical properties of the body part.

According to an aspect of some embodiments of the present invention there is provided a method for physically reconstructing a body part using multi-material additive manufacturing, the method comprising: receiving image data of the body part in the form of arrays of voxels, each array of voxels representing image data pertaining to cross-section of the body part; translating the image data in the arrays of voxels to printable bitmap images representing combinations of modeling materials for reconstructing the body part; and dispensing the combinations of modeling materials responsive to the bitmap images in a layerwise manner.

Optionally, the method includes defining a relationship between voxel values in the array of voxels and target physical properties for reconstructing the body part; defining a relationship between combinations of modeling materials and their physical properties; and defining a relationship between the voxel values and the material combination responsive to the relationship defined between the voxel values and the target physical properties and the relationship defined between the combinations of modeling materials and their physical properties.

Optionally, the relationship is defined by one or more lookup tables.

Optionally, the combinations of modeling materials are selected to mimic mechanical properties of the body part on a per voxel basis.

Optionally, the image data in the arrays of voxels is translated into an array of digital materials, each digital material formed with a combination of at least two modeling materials, the combination defined by a ratio between the at least two modeling materials.

Optionally, the image data in the arrays of voxels is translated into an array of digital materials, each digital material defined as a pattern of modeling material voxels, the pattern formed with at least two different modeling materials.

Optionally, each of the digital materials in the array of digital materials is defined with a pre-defined number of modeling material voxels.

Optionally, the pre-defined number is selected from a range between 10-1000 modeling material voxels.

Optionally, different digital materials in the array of digital material are defined to have different mechanical properties.

Optionally, different digital materials are defined to have different elastic properties.

Optionally, the different digital materials are defined to have a modulus elasticity ranging between 0.01 MPa to 3 GPa.

Optionally, the digital material is formed from a liquid or gel volume surrounded by a stiffer material.

Optionally, the image data is received from one or more of a CT scanner, MRI and ultrasound device.

Optionally, the image data is received from a CT scanner and wherein the combinations of modeling materials is defined to simulate an array of densities represented by CT numbers obtained from the CT scanner.

Optionally, the method uses one or more additive materials to alter a physical appearance of a portion of the modeling materials in the array.

Optionally, the additive material is selected from a group including: dyes metals, ions, ceramics and bio-molecules.

Optionally, the additive material is applied responsive to user input.

Optionally, the method includes receiving input from a user; and adjusting the combinations of the modeling materials for reconstructing the body part based on the input from the user.

According to an aspect of some embodiments of the present invention there is provided a system for physically reconstructing a body part using multi-material additive manufacturing comprising: a controller operative to receive image data of the body part in the form of arrays of voxels, each array of voxels representing image data pertaining to cross-section of the body part; a processing unit operative to translate the image data in the arrays of voxels to printable bitmap images representing combinations of modeling materials for reconstructing the body part; and a multi-material additive material device for dispensing the combinations of modeling materials responsive to the bitmap images in a layerwise manner.

Optionally, the processor is operative to define a relationship between voxel values in the array of voxels and target physical properties for reconstructing the body part, to define a relationship between combinations of modeling materials and their physical properties, and to define a relationship between the voxel values and the material combination responsive to the relationship defined between the voxel values and the target physical properties and the relationship defined between the combinations of modeling materials and their physical properties.

Optionally, the system comprises a memory unit for storing at least one lookup table, database or equation operative to define a relationship between voxel values in the array of voxels and mechanical properties of the body part.

Optionally, the system comprises a memory unit for storing at least one lookup table, database or equation operative to define a relationship between voxel values in the array of voxels and combinations of modeling material that mimic a mechanical property of the body part.

Optionally, the processing unit is operative to select combinations of modeling materials that mimic mechanical properties of the body part on a per voxel basis.

Optionally, the processing unit is operative to translate the image data in the arrays of voxels into an array of digital materials, each digital material formed with a combination of at least two modeling materials, the combination defined by a ratio between the at least two modeling materials.

Optionally, each of the digital materials in the array is defined with a pre-defined number of modeling material voxels.

Optionally, the pre-defined number is selected from a range between 10-1000 modeling material voxels.

Optionally, different digital materials in the array are defined to have different mechanical properties.

Optionally, the digital material is formed from a liquid or gel volume surrounded by a stiffer material.

Optionally, the digital material is defined to have a unit size of sub-millimeter macro voxel.

Optionally, the image data is received from one more imaging devices selected from a group including a CT scanner, MRI and ultrasound device.

Optionally, the printable bitmap images include data for adding one or more additional materials to the combinations of modeling materials.

Optionally, the additional material is selected from a group including: dyes metals, ions, ceramics and bio-molecules.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to multi-material AM and, more particularly, but not exclusively, tomographic based physical reconstruction of an object such as a body part with multi-material AM.

In known methods for making a physical model of a body organ based on tomography and/or image data, a threshold approach is typically used on the image data to identify and/or differentiate between different tissues, e.g. muscle tissue and bone tissue that are imaged. Once identified, contours of each of the identified tissues are defined and used to construct a three dimensional computerized model of each of the tissues to be modeled using a polygon based file and/or an STL file. During this process, image data showing variations within the tissues and/or gradual changes at the interface between tissues are lost and/or discarded. The STL file is typically used to produce the model as an assembly of the identified tissues. Although based on this approach each of the different tissues can be constructed with a different material composition, there is no available information for mimicking variations in properties, e.g. within a single tissue and/or at an interface between tissues.

The present inventors have found that the mechanical feel and appearance of body part models can be better replicated or reconstructed by applying more of the tomography data to additional reconstruct and/or replicate gradual transitions and variations that naturally occur in the body. The present inventors have also found that mechanical properties of a body part can be replicated in a model by correlating tomography data, e.g. CT numbers with known mechanical properties of the body part and then defining combinations of different materials at the voxel level that can replicate the designated mechanical properties.

According to an aspect of some embodiments of the present invention, there is provided a system and method for physically reconstructing a body part with multi-material AM where a material composition and/or physical appearance of a body part model is determined and can be altered on a per voxel basis. Typically, three-dimensional image data e.g. tomography data, e.g. obtained from a medical imaging device such as CT scanner, Magnetic Resonance Imager (MRI), Ultrasound and Optical scanning is constructed from a matrix of voxels or a plurality of slices, each slice including a two dimensional array of voxels. The type of information provided by voxel data depends on the imaging device from which it is obtained, e.g. CT scanners provide density information and MRI provides information on H atom concentration.

According to some embodiments of the present invention, the voxel information obtained from one or more imaging devices is related to and/or associated with mechanical properties of the tissues. In some exemplary embodiment, voxel information is related to a rigidity and/or compliancy of a tissue. Typically, a relationship between tomography voxel data and mechanical property is determined based on experimental data and/or known mechanical properties of tissues, e.g. known mechanical properties of bones and ligaments.

According to some embodiments of the present invention, tomography voxel data is used by the multi-material AM device without requiring a CAD system to first construct a computerized model of the body part, for example an STL file. In some exemplary embodiments a raster file is created for each slice of image data and used as input to the multi-material AM device in place of the STL file(s). According to some embodiments of the present invention, the different voxel values within a slice of the tomography data are translated into different material compositions during the AM process. Typically, each voxel of image data is translated into a macrovoxel composed of a plurality of printing voxels, e.g. 10-1000 voxels or 300 voxels of building material. The present inventors have found that by varying the material composition based on changes in tomography voxel values, a more natural physical representation of the different tissues can be replicated including smooth transitions between different types of tissues.

The present inventors have also found that a raster-raster translation is faster, more computationally efficient and requires less software tools, because there is no need to go from raster to mesh and then back to raster, as is done with the STL approach.

According to some embodiments of the present invention, additional information can be added to produce an AM file in the form of a raster file, to include color information, organ type and/or other manually inserted information, e.g. provided by a doctor and/or other user. Optionally, color and transparency levels of different body part regions may be controlled independently to provide accurate optical simulation of the living organ's appearance. Optionally, image data from one or more imaging devices may be combined to create the raster files used as input to the multi-material AM device.

Optionally an automatic or human-aided algorithm can be used to add data for reconstructing one or more features that may be missing in the tomography data, for example due to insufficient resolution of the scan. For example, the epithelium and endothelium are usually absent in CT scans due to their small dimensions. However, their locations may be defined as an outer and/or inner boundary of the organ and data for reconstructing the epithelium and endothelium can be added. Optionally an automatic or human-aided algorithm can be used to add additional data that may improve the appearance and/or mechanical feel and/or stability of the model.

Optionally, additional data may define a color for a specific tissue, organ or region. In another example connective tissues can be automatically identified, specifically in regions where different tissues connect (e.g. bone and soft tissue). Optionally, such regions can be fabricated using gel or gel-like material e.g. support material to allow better separation between the tissues, for example when serving as a device for surgery training or other education purposes.

According to some embodiments of the present invention, the multi-material AM device operates with at least two materials, e.g. a compliant material and a stiff material.

Optionally, one or more lookup tables are used to relate the image data to data in the raster files that defines the material makeup based on the image data. Optionally a relationship between image data and material composition is defined with one or more look-up tables and/or one or more defined functions, e.g. based on experimental data or based on literature. Optionally, a relationship between image data and material composition is defined manually after experimentally relating one or more image data values, e.g. CT numbers to material properties.

Optionally, the multi-material AM device may use additional materials, including materials which remain in liquid state during the entire AM process, said liquid material permitting correct reproduction of extremely soft tissue and/or body fluids, such as blood or lymph. The materials employed may be opaque or transparent, and/or have specific coloring depending on the desired application. Moreover, the AM device can make use of additional colored and/or transparent materials for adjusting the appearance of the different regions of synthetic organ.

According to some embodiments of the present invention, a multi-material AM printer, e.g. the Connex™ system by Objet Ltd., Israel, is used to fabricate a model of a body part using two materials having different mechanical properties and different appearances, e.g. a rigid material that is opaque and a compliant material that is transparent. In some exemplary embodiments, a body part model is fabricated with a rigid opaque material used to represent dense material such as found in bone and a compliant transparent material for representing soft and/or fluidic tissues. Typically, two or more modeling materials can be used to design a variety of digital materials with a spectrum of properties, e.g. ranging between rigid bone and soft fluidic tissues.

Figure 1:
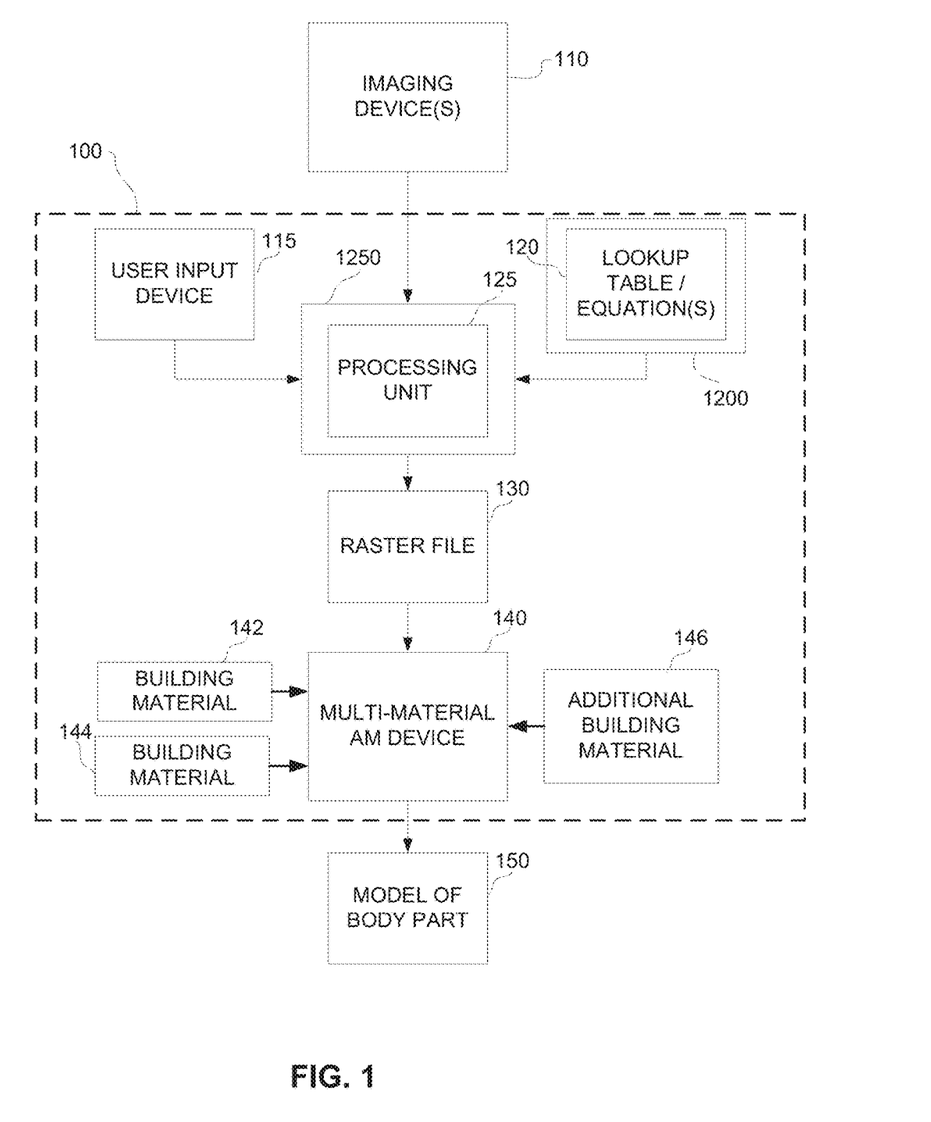
FIG. 1 is a simplified block diagram of an exemplary system for fabricating a body part using multi-material AM in accordance with some embodiments of the present invention.
Figure 2:
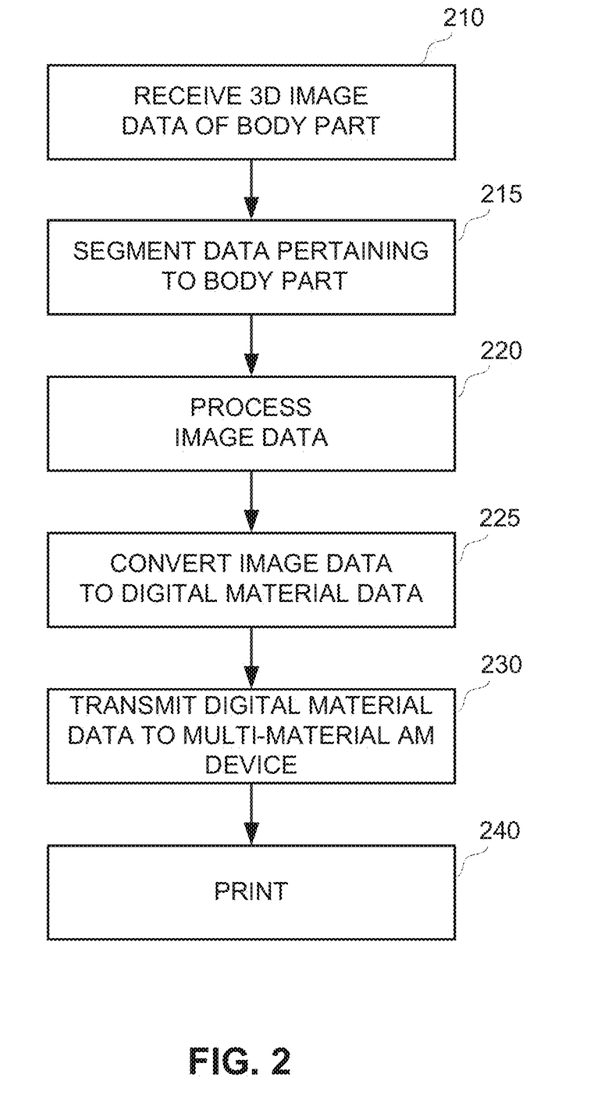
FIG. 2 is a simplified flow chart of an exemplary method for fabricating a body part using multi-material AM in accordance with some embodiments of the present invention.

Reference is now made to FIG. 1 showing a simplified block diagram of an exemplary system and to FIG. 2 showing a simplified flow chart of an exemplary method, both for fabricating a body part using multi-material AM device in accordance with some embodiments of the present invention. According to some embodiments of the present invention, a system 100 receives three dimensional image data of the body part from imaging device 110, e.g. a CT scanner, MRI, ultrasound, or optical scanner (block 210, FIG. 2). Typically, the image data is formed from a plurality of two dimensional images each image representing a slice of the body part. Typically, each slice of image data is a two dimensional array of voxels having values related to a structural and/or material characteristic of the body tissue, e.g. density of the tissue. Typically, the different voxel values provide contrast for imaging different tissues of the body but the voxels can also be used to determine material and/or physical properties of the body part at each three dimensional voxel location.

Optionally, processing unit 125 of system 100 segments image data pertaining to the body part to be modeled from the images captured (block 215, FIG. 2). Typically, processing unit 125 is associated with and/or part of a controller 1250 of system 100. Alternatively, segmentation can be performed by imaging device 110. Optionally, processing unit 125 performs image post processing to further enhance one or more features of the image, e.g. three dimensional image and/or individual image slices.

Optionally, image data is obtained from a plurality of different imaging devices 110 and processing unit 125 combines the image data from the different imaging devices.

Optionally, input from a plurality of different imaging devices is used to further enhance contrast between different soft tissues of the body. Optionally, post processing is performed for smoothing out differences in image data along a seam between different image slices.

Optionally, in addition to image data received by the processing unit, a user may provide additional information with user input device 115. Optionally, a user selects a color and/or transparency level for an identified tissue and/or organ of the body part. Optionally, a user can add a distinguishing feature to differentiate between tissues having similar image voxel values. Optionally, a user selectively employs 3D capable software for viewing and/or providing input. Optionally, a user provides input by marking images displayed by the processing unit and the image data received by the processing unit incorporates the user input.

According to some embodiments of the present invention, one or more lookup tables and/or equations or functions 120 are used by processing unit 125 to convert the original voxel values, e.g. grayscale values of the image data into material data for printing the model of the body part (block 225, FIG. 2). In some exemplary embodiments of the present invention, each voxel of image data is fabricated in the model of the body part with a plurality of voxels of building material/s, e.g. 10-1000 voxels of building material, and/or 300 voxels of building materials. As used herein, digital material is a material formed from a predefined number of voxels of different building materials that are deposited in a contiguous manner and optionally solidified during the AM building process to form a third material (i.e. a digital material). The different properties of each material provide for obtaining multi-material combinations having a range of properties between the properties of each of the parent materials as a result of their spatial combination and ratio of their combination. Optionally, the digital material is formed over a plurality of printing layers. Optionally, pre-defined digital material combinations are used rather than pseudo-random mixes. In such case each region having a same image voxel value is replaced by a bitmap from a predefined composition that is linked to that voxel value in a lookup table. Optionally, when the resolution of the image voxel data is higher than the building material voxel, a different approach can be used, for example error propagation dithering method can be used.

Optionally a support material may take part in the digital material composition. Digital material is described in further detail herein below, e.g. in reference to FIG. 4A-4E. Optionally, properties of the digital material are defined to closely resemble a material and/or physical properties of the tissue that is imaged. Typically, variations in the material properties of the model can be varied on a per voxel basis by altering the constituents and/or the proportions of the constituents of the digital material. Typically, one or more lookup tables and/or equations 120 are stored in a memory unit 1200 of system 100. Optionally the lookup table is a database, e.g. a building material database. Optionally, when the image data is in the form of a gray scale, the lookup table provides a relationship between gray scale values and material composition. For example, a gray level of 128 may optionally correspond to 30% compliant material and 70% stiff material.

According to some embodiments of the present invention, a raster file (130) including a bitmap of the digital material data is created for each slice of image data and transmitted to multi-material AM device 140 (block 230, FIG. 2) based on which the model is printed one layer at a time (block 240, FIG. 2). Typically, one slice of image data is replicated with a plurality of printed layers, e.g. 5-20 printing layers. Typically, a plurality of raster files, e.g. one for each image data slice is transmitted to the multi-material AM device for printing full model of the body part 150.

According to some embodiment of the present invention, multi-material AM device 140 is equipped with at least two building materials, each with different mechanical properties, e.g. building material 142 and building material 144 that can be dispensed in different proportions and/or patterns to simulate a spectrum of mechanical properties that can be used to replicate variations in properties of the body part. Optionally, multi-material AM device 140 is equipped with additional material, e.g. material 146 that can be used independently from building material 142 and 144 to simulate color, e.g. a dye and/or transparency levels of different regions in the body part, or enhance other physical features of the body part. Optionally, additive materials are used to simulate spatial distribution of contrast agents used during medical imaging. Additional materials may include for example metals, ions, ceramics, bio-molecules and other active substances.

Figure 3:
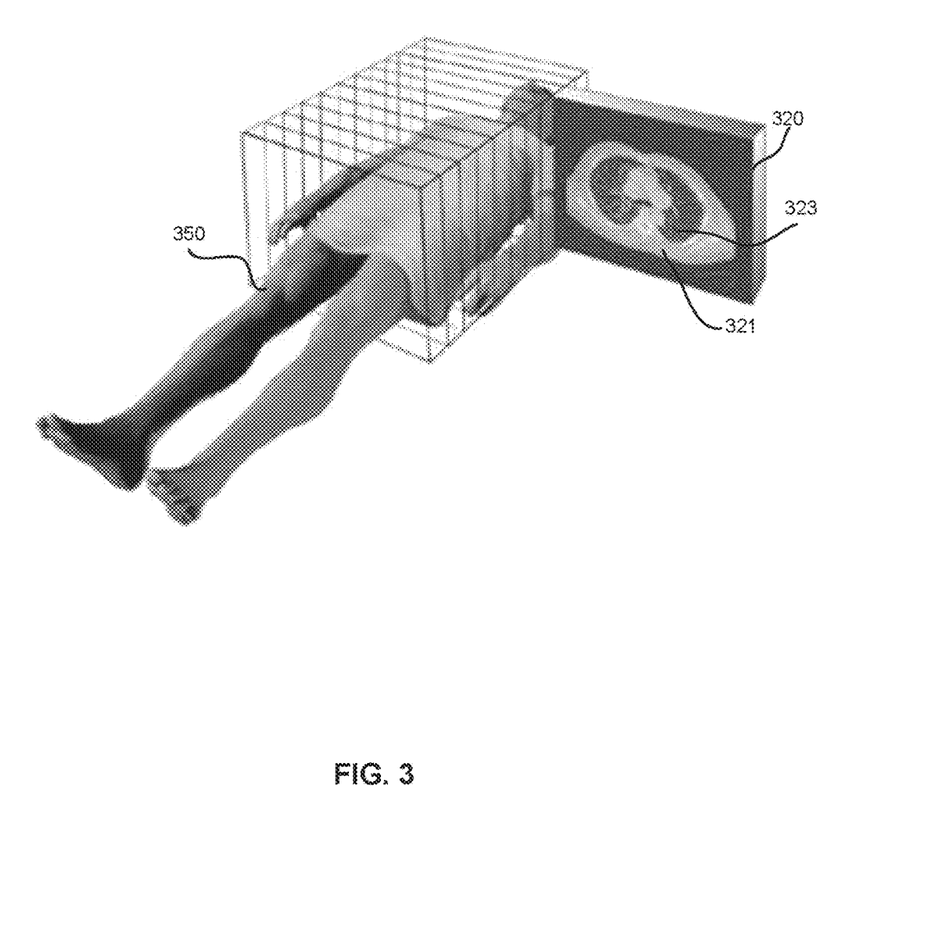
FIG. 3 is an exemplary slice of image data obtained with a CT scanner that can be used to fabricate a body part model of a spine with multi-material AM in accordance with some embodiments of the present invention.

Reference is now made to FIG. 3 showing an exemplary slice of image data obtained with a CT scanner that can be used to fabricate a body part model of a spine with multi-material AM in accordance with some embodiments of the present invention. According to some embodiments of the present invention, a model of a spine (or a portion of a spine) is formed from images obtained from one or more CT image slices 320 captured from a person. Typically, CT images include brighter regions 321 reflected from hyper-dense material and darker regions 323 reflected from hypo-dense structures, e.g. soft tissues or liquid material defined by a two dimensional array of CT numbers.

Optionally, the CT number may be correlated to the Young's modulus of the corresponding region of the scanned tissue and a model of the spine as imaged may be fabricated by combining a rigid and/or a stiff building material and a compliant, e.g. flexible and/or elastic building material in different proportions. Optionally, brighter regions 321 are modeled with a high percentage of rigid and/or stiff building material while darker regions 323 are modeled with a high percentage of compliant and/or elastic building material. Typically, a proportion between the two or more building materials used to model each voxel is defined by the CT number of a voxel and by known mechanical properties of the stiffest and most compliant material imaged. Optionally, the stiffness of the stiff material is chosen to be similar or greater than the stiffness of the stiffest tissue to be simulated and the stiffness of the compliant building material is chosen to be close to or less than the stiffness of the most compliant material. By varying the proportions between the two or more building materials a broad spectrum of mechanical properties can be simulated.

Optionally, additional materials which remain in liquid state during the entire AM process may be used to simulate the darkest regions. Optionally, the liquid material is used to simulate very soft tissue and/or body fluids, such as blood or lymph. The building materials used may be opaque or transparent, and/or have specific coloring depending on the desired application. Moreover, the AM system can make use of additional colored and/or transparent materials for adjusting the appearance of the different regions of the model.

Optionally, gel regions can be formed within a mode to simulate properties of soft tissues or properties of endothelial surfaces, e.g. epithelial tissue that covers organ surfaces. Optionally a hydrophilic UV curable resin can be used to form hydrophilic material. Optionally, upon immersion in aqueous solution, the material will absorb water and swell to form smooth and soft gel that may mimic some of the body's natural soft tissues, e.g. epithelium tissue.

Reference is now made to FIGS. 4A, 4B, 4C, 4D and 4E showing exemplary illustrative representations of different material patterns in accordance with some embodiments of the present invention. According to some embodiments of the present invention, a digital material is a material that is formed with small volumes, e.g. drops of different building materials 410 and 420 that are deposited simultaneously and optionally solidified during an AM building process. Digital materials may be formed in dimensions of unit cells or macro voxels. The unit cell and/or macro voxel is defined herein as the smallest volume of digital material that has the defined material properties of the digital material. Optionally, the unit size of the macro voxel corresponds to the unit size represented by one voxel of image data.

Typically, the different building materials have different mechanical properties, e.g. stiffness, flexibility, density, color, transparency, water absorption (%), solvent absorption (%), non-polymerized liquid fraction, nano-particles fraction. Optionally and/or additionally, a digital material is formed by dispensing different building materials over a plurality of different layers. In some exemplary embodiments, the mechanical properties of a digital material are set by defining a ratio between different building materials used to form the digital material. In some exemplary embodiments, a digital material is defined to have a unit size of a millimeter or sub-millimeter macro voxel and each macro voxel contains tens or hundreds of dispensed drops of building material, e.g. 10-1000 micro voxels.

Figure 4A:
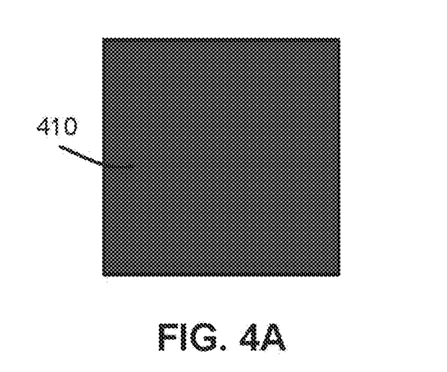
FIGS. 4A, 4B, 4C, 4D and 4E are exemplary illustrative representations of different digital material patterns in accordance with some embodiments of the present invention.
Figure 4B:
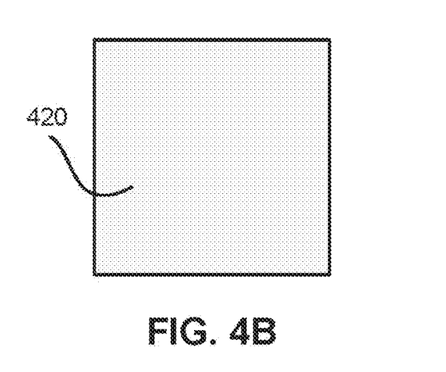
Figure 4C:
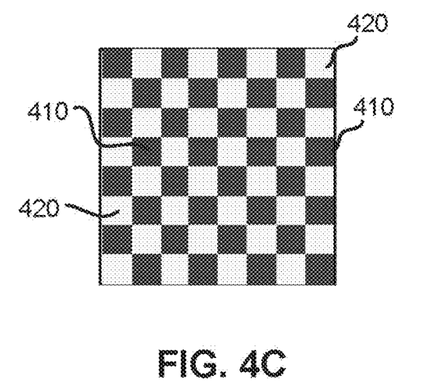
Figure 4D:
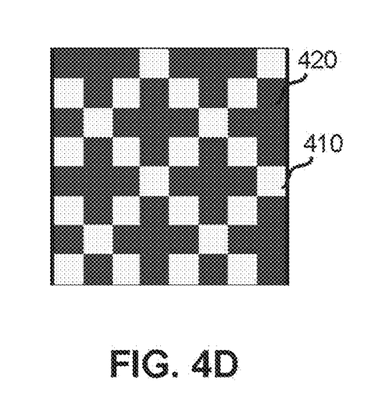
Figure 4E:
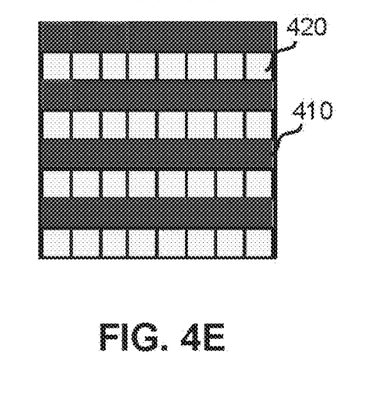

In some exemplary embodiments, the geometrical and/or spatial pattern in which the constituents are dispensed may vary according to the desired mechanical and/or physical properties desired. Typically, the spatial pattern of such deposition can be random or pseudo random (FIG. 4D), but in some cases a structured pattern may be desired (FIGS. 4C and 4E). Optionally, a single building material, e.g. single building material 410 (FIG. 4A) or single building material 420 (FIG. 4B) may be used alone to replicate a high or highest level of a given property.

In some exemplary embodiments, a body part model is formed with one stiff and/or rigid material RGD535™, RGD525™, FullCure®720, all available by Objet Ltd., Israel and/or compliant material Objet TangoPlus™, TangoBlackPlus™, TangoBlack™, TangoGrey™, all available by Objet Ltd., Israel. Optionally, the stiffness of the stiff material is chosen as a material that has a stiffness that is similar to or greater than a stiffness of the stiffest tissue to be simulated and the stiffness of the compliant or flexible material is chosen as a material that is similar to or less than that of the least stiff tissue to be simulated. Typically, the modulus of elasticity of body tissues varies between about 0.01 MPa to about 3 GPa. The present inventors have found that the mechanical behavior or characteristics of most organs and/or body parts can be simulated when fabricating the model with one material have a modulus of elasticity of body tissues of about 0.01 MPa and another material with a modulus of elasticity of body tissues varies between about 3 GPa.

Optionally, the digital material is not required to be formed using a pre-defined pattern of modeling material. Rather, the digital material can be defined by a ratio between two or more modeling materials, e.g. parent materials to be pseudo-randomly mixed on the print voxel level. This case typically requires significantly smaller computational resources since the printing voxels can be assigned on-the-fly by randomly dispensing the voxels according to the required mix ratio. Another advantage of pseudo-random mixing is that dispensing can take place on a per slice basis without requiring a Z-buffer to reference pattern on alternate slices.

Figure 5A:
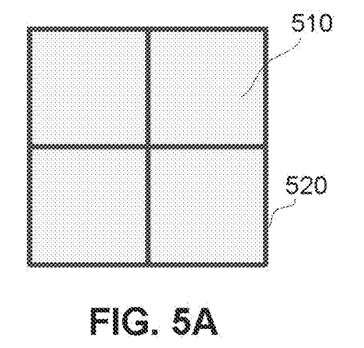
FIGS. 5A, 5B and 5C are exemplary compartmental digital material structures where a liquid material is surrounded by the rubber like material.
Figure 5B:
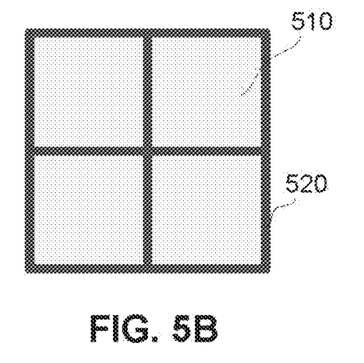
Figure 5C:
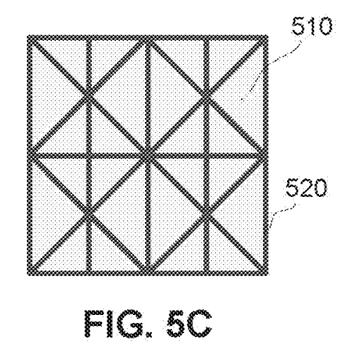

Reference is now made to FIGS. 5A, 5B and 5C showing exemplary compartmental digital material structures where a liquid material is surrounded by the rubber like material. In some embodiments a digital material unit cell is defined as compartment; a liquid or gel volume surrounded by a stiffer material. Different compartmental unit cells can be defined to produce different mechanical behaviors. In some exemplary embodiments, a very soft gel e.g. having a compressive modulus below 0.1 MPa, liquid, and/or non-solidifying materials 510 is used to simulate soft tissues, connective tissues, blood vessels and other body organs that contain a high fraction of liquids. The present inventors have found that leakage of liquid materials can occur during or after the 3D object fabrication. In some exemplary embodiments, leakage is avoided by fabricating millimeter or sub-millimeter compartmental structures, where each portion of the liquid or soft gel material is surrounded or encapsulated by other solid material, rubber-like building material or digital material, e.g. polyethylene glycol 400 (PEG400), surrounded by a TangoPlus rubber-like material.

In some exemplary embodiments, the stiffness of a compartmental digital material structure is controlled by controlling overall rubber/liquid ratio, compartment size, wall thickness, stiffness of the rubber-like material, introduction of additional rubber-like filaments or partitions to "reinforce" the liquid region. Optionally, increased stiffness is achieved by increasing thickness of rubber-like building material 520 (FIG. 5B as compared to FIG. 5A). Optionally, increased stiffness is achieved by decreasing the defined size of the compartment and/or by changing shape of the compartments (FIG. 5C). Optionally, triangular shaped compartments as shown in FIG. 5C are more durable than square shaped compartments shown in FIGS. 5A and 5B. Optionally, the compartments structure may mimic the structure of living body cells.

Figure 6A:
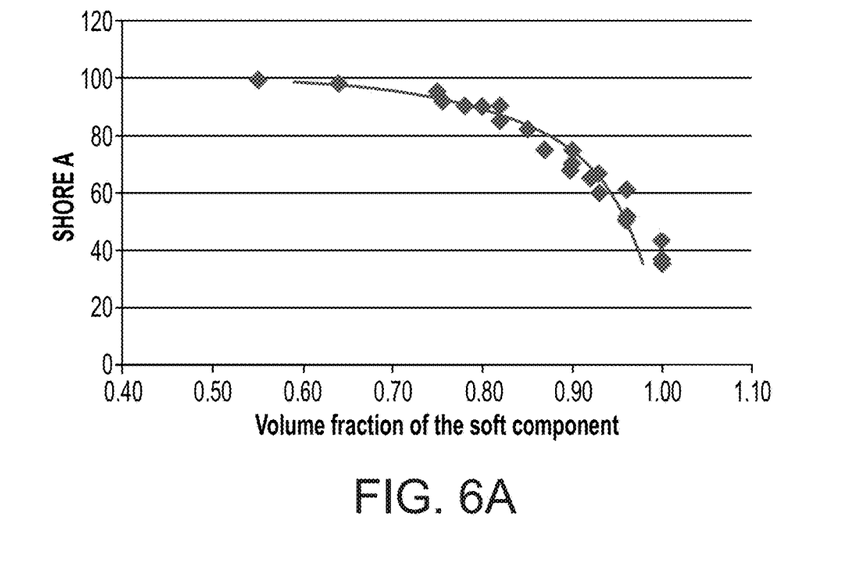
FIGS. 6A and 6B are exemplary graphs of calibration curves for producing a digital material with one soft material and one rigid material in accordance with some embodiments of the present invention.
Figure 6B:
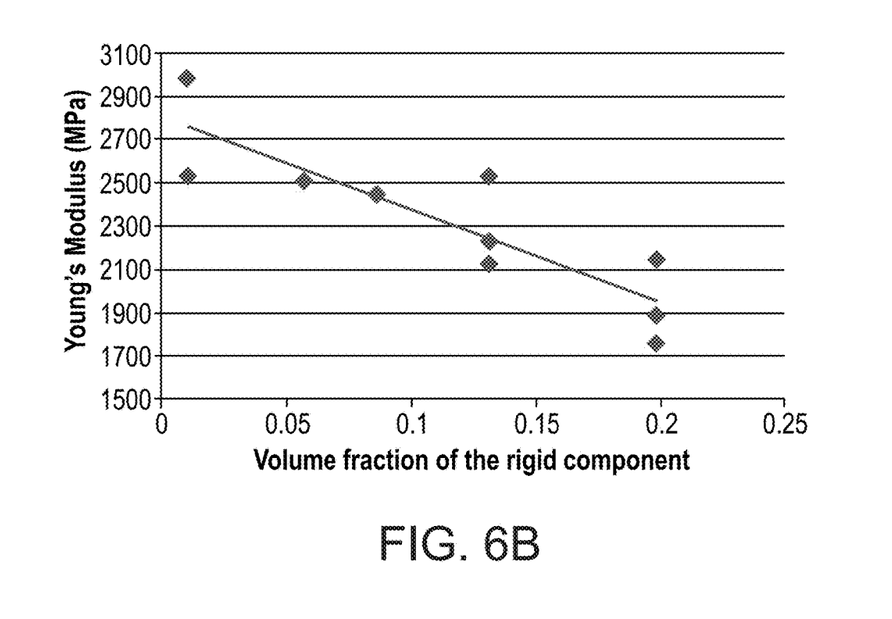

Reference is now made to FIGS. 6A and 6B showing exemplary graphs of calibration curves for digital materials composed with one soft material (TangoBlackPlus™) and one rigid material (RGD525™) that can be used in accordance with some embodiments of the present invention. FIG. 6A is an exemplary graph showing a SHORE-A value of a digital material as a function of volume fraction of the soft material in a digital material. FIG. 6B is an exemplary graph showing a Young's modulus of a digital material as a function of volume fraction of the rigid material in a digital material. The triangular points on the graph represent experimental data and the curve represents an exemplary analytical fit. Optionally, an analytic fit can be used to define one or more equations relating a physical property of a body part in a defined location as determined from imaging and constituents of a digital material to mimic the physical property. Optionally, user input is additionally used to define a physical property of an identified element of a body part.

Figure 7A:
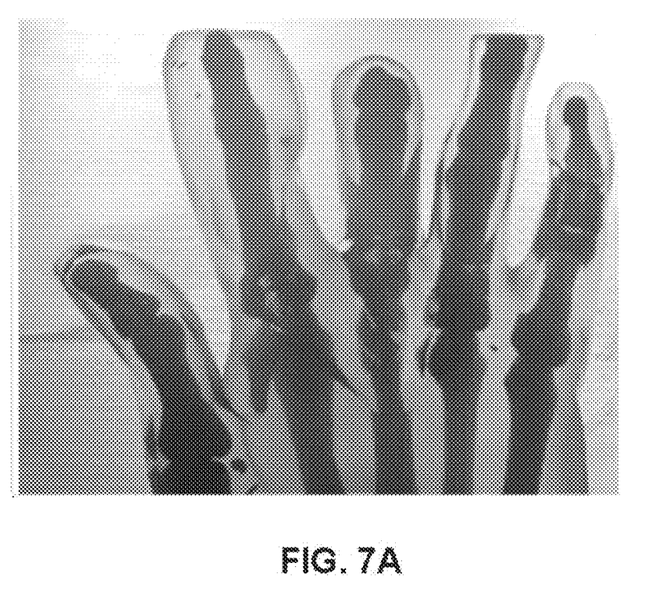
FIGS. 7A and 7B show an exemplary reconstruction of a hand using a known AM method (FIG. 7A) and using a method in accordance in accordance with some embodiments of the present invention (FIG. 7B).
Figure 7B:
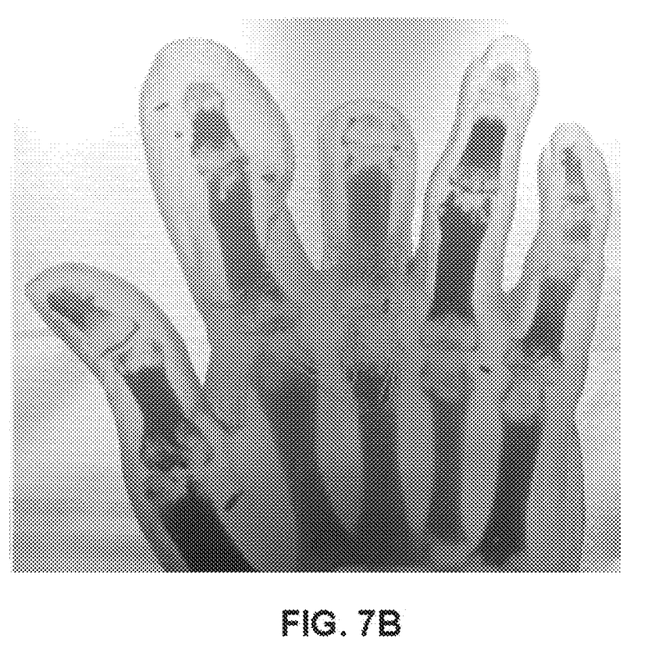

Reference is now made to FIGS. 7A and 7B showing exemplary reconstructions of a hand. FIG. 7A shows reconstruction of a hand using two modeling materials, black material and a clear material, by a known AM technique using STL files, where black material indicates bone and clear material indicates non-bone tissue. In comparison, FIG. 7B shows an exemplary physical reconstruction of a hand using a system and method in accordance with some embodiments of the present invention. As can be seen in FIG. 7B, a hand has been reconstructed with varying combinations of two modeling materials, black material and a clear material. Black was used for the most rigid areas and clear for the most compliant areas, and varying spatial combinations of differing ratios of the two materials are used to replicate varying properties in or within different areas. Thus, by using the system and method in accordance with some embodiments of the present invention, variations in the properties of the bone for example in the joint area have been reconstructed and the joint area has been differentiated.

It is noted that although most of the embodiments have been described in reference to fabricating a model of a body part, the embodiments of the present invention are not limited in that respect and that the same system and methods can be used for fabricating models of other objects formed from a plurality of different materials.

It is further noted that although most of the embodiments have been described in reference to fabricating a model of a body part using a combination of stiff and compliant material, the embodiments of the present invention are not limited in that respect. In other embodiments of the present invention, a model of a body part can be fabricated using a combination of building materials have various different mechanical and/or physical properties to mimic the properties of the body part.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A method for physically reconstructing an object using multi-material additive manufacturing, the method comprising:
   receiving tomography data of the object from one or more of a CT scanner, MRI and ultrasound device, wherein the tomography data is in the form of arrays of tomography voxels, each array pertaining to a cross-section of the object and each tomography voxel having a value;
   defining a relationship between tomography voxel values and target physical properties for reconstructing the object;
   defining a relationship between combinations of modeling materials and their physical properties; and
   defining a relationship between tomography voxel values and the material combination responsive to the relationship defined between the voxel values and the target physical properties and the relationship defined between the combinations of modeling materials and their physical properties;
   translating tomography data to printable bitmap images representing combinations of modeling materials for reconstructing the object; and
   dispensing the combinations of modeling materials responsive to the bitmap images in a layerwise manner, wherein the combinations of modeling materials in each layer are dispensed in a dropwise manner with an additive manufacturing device;
   wherein the translating of the tomography data to the printable bitmap images is by raster-raster translation.

2. The method according to claim 1, wherein the relationship between the voxel values and the material combination is defined by one or more lookup tables.

3. The method according to claim 1, wherein the combinations of modeling materials are selected to mimic mechanical properties of the object on a per voxel basis.

4. The method according to claim 1, wherein the tomography data in the arrays of voxels is translated into an array of digital materials, each digital material formed with a combination of at least two modeling materials.

5. The method according to claim 4, wherein each of the digital materials in the array of digital materials is defined with a pre-defined number of modeling material voxels.

6. The method according to claim 4, wherein different digital materials in the array of digital materials are defined to have different mechanical properties.

7. The method according to claim 6, wherein different digital materials are defined to have different elastic properties.

8. The method according to claim 4, wherein the digital material is formed from a liquid or gel volume surrounded by a stiffer material.

9. The method of claim 1, wherein the combinations of modeling materials are defined to simulate an array of densities represented by CT numbers obtained from the CT scanner when the tomography data is received from a CT scanner.

10. The method of claim 1, using one or more additional materials to alter a physical appearance of a portion of the modeling material.

11. The method of claim 10, wherein the additional material is applied responsive to user input.

12. The method of claim 1, comprising:
   receiving input from a user; and
   adjusting the combinations of the modeling materials for reconstructing the object based on the input from the user.

13. A method for physically reconstructing an object using multi-material additive manufacturing, the method comprising:
   receiving image data of the object from one or more of a CT scanner, MRI and ultrasound device, in the form of arrays of image voxels, each array pertaining to a cross-section of the object and each image voxel having a value;
   defining a relationship between image voxel values and target physical properties for reconstructing the object;
   defining a relationship between combinations of modeling materials and their physical properties; and
   defining a relationship between the image voxel values and the material combination responsive to the relationship defined between the voxel values and the target physical properties and the relationship defined between the combinations of modeling materials and their physical properties;
   translating the image voxel values to printable bitmap images representing combinations of modeling materials for reconstructing the object, wherein the translating is by raster-raster translation; and
   dispensing the combinations of modeling materials responsive to the bitmap images in a layerwise manner, wherein the combinations of modeling materials in each layer is dispensed in a dropwise manner with an additive manufacturing device.

14. The method of claim 1, wherein the object is a body part.

15. The method of claim 1, wherein the tomography voxel value is a gray scale value.

16. The method of claim 1, wherein the tomography voxel data is used by the multi-material additive manufacturing device without requiring a CAD system to first construct a computerized model of the body part.

17. The method of claim 1, wherein at least one of the modeling materials is configured to remain in liquid state during the entire AM process.

18. The method of claim 17, wherein the at least one of the modeling materials is configured to provide reproduction of at least one of extremely soft tissue and body fluids.

19. The method of claim 17, wherein the at least one of the modeling materials may be selected to have one of a plurality of different colors supported by the additive manufacturing device.

* * * * *